(12) United States Patent
Spencer et al.

(10) Patent No.: US 10,160,817 B2
(45) Date of Patent: Dec. 25, 2018

(54) ETHYLENE BASED INTERPOLYMERS AND COMPOSITION COMPRISING THE SAME

(71) Applicant: Dow Global Technologies LLC, Midland, MI (US)

(72) Inventors: Liam P. Spencer, Freeport, TX (US); Sean W. Ewart, Freeport, TX (US); David M. Pearson, Freeport, TX (US); Lixin Sun, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/535,576

(22) PCT Filed: Dec. 23, 2015

(86) PCT No.: PCT/US2015/000163
§ 371 (c)(1),
(2) Date: Jun. 13, 2017

(87) PCT Pub. No.: WO2016/105454
PCT Pub. Date: Jun. 30, 2016

(65) Prior Publication Data
US 2017/0369609 A1 Dec. 28, 2017

Related U.S. Application Data

(60) Provisional application No. 62/095,811, filed on Dec. 23, 2014.

(51) Int. Cl.
| | |
|---|---|
| *C08F 210/02* | (2006.01) |
| *C08F 4/6592* | (2006.01) |
| *C08G 81/02* | (2006.01) |
| *C08F 299/00* | (2006.01) |
| *C08F 4/659* | (2006.01) |
| *C08F 212/32* | (2006.01) |
| *C08F 12/12* | (2006.01) |
| *C08F 210/16* | (2006.01) |
| *G01N 33/46* | (2006.01) |
| *G01N 30/00* | (2006.01) |

(52) U.S. Cl.
CPC .......... *C08F 210/02* (2013.01); *C08F 4/6592* (2013.01); *C08F 299/00* (2013.01); *C08G 81/02* (2013.01); *C08F 4/65908* (2013.01); *C08F 4/65912* (2013.01); *C08F 12/12* (2013.01); *C08F 210/16* (2013.01); *C08F 212/32* (2013.01); *C08F 2420/02* (2013.01); *G01N 33/46* (2013.01); *G01N 2030/486* (2013.01)

(58) Field of Classification Search
CPC .... C08F 210/02; C08F 299/00; C08F 4/6592; C08F 210/16; C08F 12/12; C08F 4/65912; C08F 2420/02; C08F 212/32; C08G 81/02; G01N 33/46; G01N 2030/486

See application file for complete search history.

(56) References Cited

U.S. PATENT DOCUMENTS

| | | | |
|---|---|---|---|
| 4,622,375 A * | 11/1986 | Wong | C08F 210/16 526/169.2 |
| 5,844,045 A | 12/1998 | Kolthammer et al. | |
| 5,869,575 A | 2/1999 | Kolthammer et al. | |
| 6,448,341 B1 | 9/2002 | Kolthammer et al. | |
| 6,538,070 B1 | 3/2003 | Cardwell et al. | |
| 6,545,088 B1 | 4/2003 | Kolthammer et al. | |
| 6,566,446 B1 | 5/2003 | Parikh et al. | |

FOREIGN PATENT DOCUMENTS

EP 0227142 A1 7/1987

OTHER PUBLICATIONS

Williams, T., et al., J. Polym. Sci., Polym. Let., vol. 6, pp. 621-624 (1968).

* cited by examiner

*Primary Examiner* — Robert D. Harlan
(74) *Attorney, Agent, or Firm* — Husch Blackwell LLP

(57) ABSTRACT

A first ethylene-based interpolymer comprising, in polymerized form, monomer units derived from ethylene and from a benzocyclobutene (VBCB) structure of Structure 1; wherein n is from 3 to 10; and wherein the ethylene-based polymer comprises, in polymerized form, from 0.02 to 0.70 wt % of the Structure 1, based on the weight of the first ethylene-based interpolymer, as determined by $^1$H NMR is provided. Further provided is a composition which comprises a second ethylene-based inter-polymer formed by thermally treating a first ethylene-based interpolymer.

11 Claims, 2 Drawing Sheets

ETHYLENE BASED INTERPOLYMERS AND COMPOSITION COMPRISING THE SAME

REFERENCE TO RELATED APPLICATIONS

This application is a PCT Application of U.S. Provisional Application Ser. No. 62/095,811, filed Dec. 23, 2014, the disclosures of which are incorporated herein by reference.

BACKGROUND

One technical solution to increase long chain branching in a polymer chain is to introduce an α-ω diene like 1,9 decadiene (DD) that, once incorporated in a chain, can connect two chains together and form a H-type branch. One issue with this technology, however, is to avoid forming gels in the reactor as multiple branch-on-branch networks can be formed with the cross-linking reactions.

EP 0227142A2 discloses polymers of a benzocyclobutene and processes for making them. The end product disclosed in this reference contain randomly distributed benzocyclobutene structures in the styrene end blocks.

The present invention addresses this issue by formation of H-branches via post-reactor processes at temperatures greater than the reactor temperature.

SUMMARY OF THE INVENTION

The invention provides a first ethylene-based interpolymer comprising, in polymerized form, monomer units derived from ethylene and optionally, one or more alpha-olefin monomers, and from the vinyl benzocyclobutene (VBCB) structure of Structure 1:

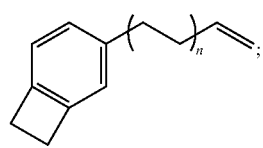

(Structure 1)

wherein n is from 3 to 10; and
wherein the ethylene-based polymer comprises, in polymerized form, from 0.02 to 0.70 wt % of the Structure 1, based on the weight of the ethylene-based interpolymer, as determined by $^1$H NMR.

DETAILED DESCRIPTION

Figure 1:
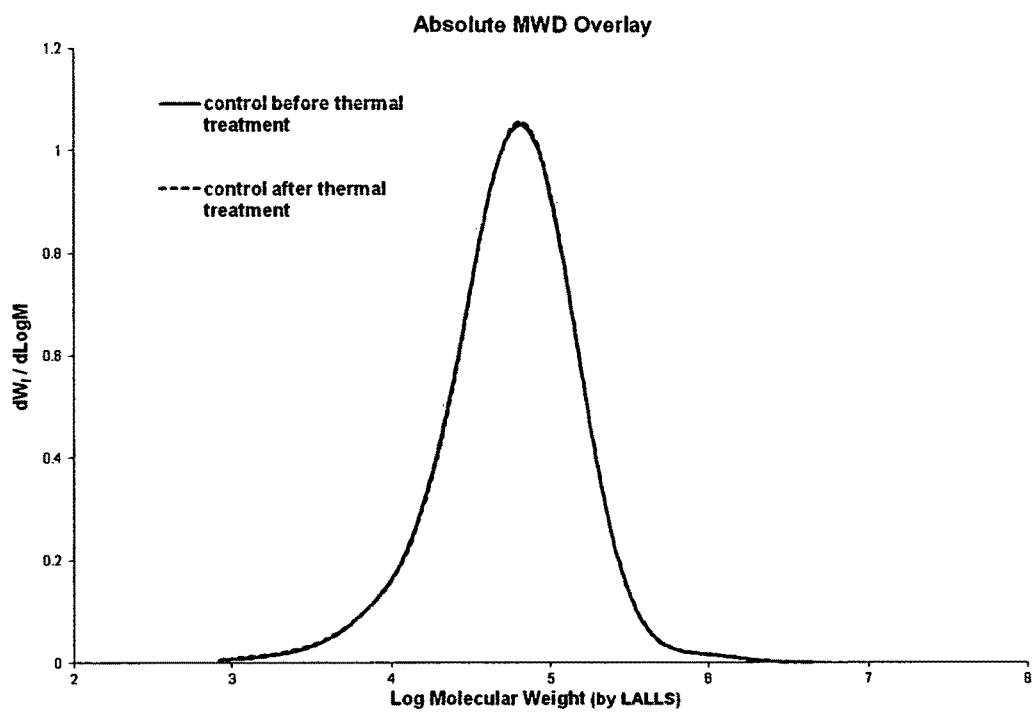
FIG. 1 is a gas phase chromatography overlay of the control sample before and after thermal treatment.

As discussed above, the invention provides a first ethylene-based interpolymer comprising, in polymerized form, monomer units derived from ethylene and optionally, one or more alpha-olefin monomers, and from the vinyl benzocyclobutene (VBCB) structure of Structure 1:

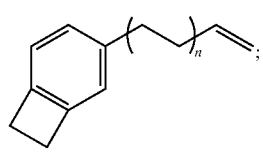

(Structure 1)

wherein n is from 3 to 10; and
wherein the ethylene-based polymer comprises, in polymerized form, from 0.02 to 0.70 wt % of the Structure 1, based on the weight of the ethylene-based interpolymer, as determined by $^1$H NMR.

In the VBCB Structure 1, n is from 3 to 10. All individual values and subranges from 3 to 10 are included and disclosed herein; for example, n can range from a lower limit of 3, 5, 7 or 9 to an upper limit of 4, 6, 8 or 10. For example, n may be from 3 to 10, or in the alternative, from 3 to 6, or in the alternative, from 6 to 10, or in the alternative, from 3 to 8.

The first ethylene-based interpolymer comprises, in polymerized form, from 0.02 to 0.70 wt % of the VBCB of Structure 1, based on the weight of the first ethylene-based interpolymer. All individual values and subranges from 0.02 to 0.70 wt % are included and disclosed herein; for example, the amount of units derived from BCB Structure 1 may range from a lower limit of 0.02, 0.08, 0.20, 0.31, 0.42, 0.53, or 0.65 wt % to an upper limit of 0.05, 0.11, 0.24, 0.35, 0.46, 0.57, 0.66 or 0.70 wt %. For example, the amount of units derived from BCB Structure 1 may be from 0.02 to 0.70 wt %, or in the alternative, from 0.30 to 0.60 wt %, or in the alternative, from 0.04 to 0.50 wt %, or in the alternative, from 0.22 to 0.630 wt %, all based on the weight of the first ethylene-based interpolymer.

The invention further provides a composition comprising a second ethylene-based interpolymer formed by thermally treating the first ethylene-based polymer. The second ethylene-based interpolymer may comprise a combination of two or more embodiments as described herein.

The disclosure further provides the first ethylene-based polymer and the composition in accordance with any embodiment disclosed herein except that the first ethylene-based interpolymer comprises greater than 50 wt % units, in polymerized form, derived from ethylene, based on the weight of the first ethylene-based polymer. All individual values and subranges from greater than 50 wt % are included and disclosed herein. For example, the amount of units, in polymerized form, derived from ethylene in the first ethylene-based polymer may be greater than 50 wt %, or in the alternative, greater than 60 wt %, or in the alternative, greater than 70 wt %, or in the alternative, greater than 80 wt %, or in the alternative, greater than 90 wt %, or in the alternative, greater than 95 wt %, or in the alternative, greater than 98 wt %, or in the alternative, greater than 99 wt %, or in the alternative, greater than 99.8 wt %, all based on the weight of the first ethylene-based polymer.

The disclosure further provides the first ethylene-based polymer and the composition in accordance with any embodiment disclosed herein except that the first ethylene-based interpolymer comprises units, in polymerized form, derived from at least one alpha-olefin monomer. Alpha-olefin monomers include, but are not limited to $C_3$-$C_{20}$ alpha-olefin monomers. In a particular embodiment, the first ethylene-based interpolymer comprises, in polymerized form, units derived from one or more of $C_3$-$C_{10}$ alpha-olefin monomers. In another embodiment, the first ethylene-based interpolymer comprises, in polymerized form, units derived from one or any combination of propylene, 1-hexene, 1-octene, (5-ethylidene-2-norbornene, 5-vinyl-2-norbornadiene, and dicyclopentadiene)

The disclosure further provides the first ethylene-based polymer and the composition in accordance with any embodiment disclosed herein except that the first ethylene-based interpolymer comprises units, in polymerized form, derived from ethylene and from 1-octene.

In one embodiment, the first ethylene-based interpolymer is an ethylene/benzocyclobutene copolymer.

In one embodiment, the first ethylene-based interpolymer is an ethylene/vinylbenzocyclobutene copolymer.

The first ethylene-based interpolymer may comprise a combination of two or more embodiments as described herein.

The second ethylene-based interpolymer is formed by thermally treating an embodiment of the first ethylene-based interpolymer. As used herein, "thermally treating" means heating at temperatures greater than 150° C. under an inert, oxygen free atmosphere, such as under nitrogen, argon, helium, or mixtures thereof. All individual values and subranges from greater than 150° C. are included and disclosed herein. For example, the temperature may be raised to greater than 150° C., or in the alternative, to greater than 175° C., or in the alternative, to greater than 200° C., or in the alternative, to greater than 225° C., or in the alternative, greater than 300° C. In a particular embodiment, the temperature is raised no higher than 350° C. In a particular embodiment, the thermal treating comprises heating the first ethylene-based interpolymer to a temperature greater than the DSC melting temperature of the first ethylene-based interpolymer.

In a particular embodiment, the first ethylene-based interpolymer is thermally treated at a temperature above the highest melting temperature (as measured by DSC) of the first ethylene-based interpolymer.

The second ethylene-based interpolymer may comprise a combination of two or more embodiments as described herein.

The disclosure further provides the first ethylene-based polymer and the composition in accordance with any embodiment disclosed herein except that the weight average molecular weight, Mw, of the first ethylene-based polymer is from 20,000 to 150,000 g/mole. All individual values and subranges from 20,000 to 150,000 g/mole are included and disclosed herein; for example, the Mw of the first ethylene-based polymer may range from a lower limit of 85,000; 87,000; 89,000; 91,000; or 93,000 g/mole to an upper limit of 86,000; 88,000; 90,000; 92,000, 94,000; or 95,000 g/mole. For example, the Mw of the first ethylene-based polymer can be from 85,000 to 95,000 g/mole, or in the alternative, from 85,000 to 90,000 g/mole, or in the alternative, from 90,000 to 95,000 g/mole, or in the alternative, from 80,000 to 100,000 g/mole.

The disclosure further provides the first ethylene-based polymer and the composition in accordance with any embodiment disclosed herein except that the weight average molecular weight, Mw, of the second ethylene-based polymer is from 50,000 to 350,000 g/mole. All individual values and subranges from 92,000 to 300,000 g/mole are included and disclosed herein; for example, the Mw of the second ethylene-based polymer may range from a lower limit of 92,000; 100,000; 150,000; 200,000; or 250,000 g/mole to an upper limit of 98,000; 125,000; 175,000; 225,000; 275,000 or 300,000 g/mole. For example, the Mw of the second ethylene-based polymer can be from 92,000 to 300,000 g/mole, or in the alternative, from 92,000 to 200,000 g/mole, or in the alternative, from 200,000 to 300,000 g/mole, or in the alternative, from 150,000 to 250,000 g/mole.

The disclosure further provides the first ethylene-based polymer and the composition in accordance with any embodiment disclosed herein except that the number average molecular weight, Mn, of each of the first ethylene-based polymer and the second ethylene-based polymer are from 10,000 to 100,000 g/mole. All individual values and subranges from 10,000 to 100,000 g/mole are included and disclosed herein; for example, the Mn of each of the first and second ethylene-based polymers range independently from a lower limit of 10,000; 20,000; 30,000; 40,000; 50,000; 60,000; 70,000; 80,000 or 90,000 g/mole to an upper limit of 20,000; 30,000; 40,000; 50,000; 60,000; 70,000; 80,000; 90,000 or 100,000 g/mole. For example, the Mn of the first ethylene-based polymer, Mn(first), can be from 10,000 to 100,000 g/mole, or in the alternative, from 10,000 to 60,000 g/mole, or in the alternative, from 50,000 to 100,000 g/mole, or in the alternative, from 30,000 to 80,000 g/mole. For example, the Mn of the second ethylene-based polymer, Mn(second), can be from 10,000 to 100,000 g/mole or in the alternative, from 10,000 to 55,000 g/mole, or in the alternative, from 60,000 to 100,000 g/mole, or in the alternative, from 25,000 to 85,000 g/mole.

The disclosure further provides the first ethylene-based polymer and the composition in accordance with any embodiment disclosed herein except that the weight average molecular weight, Mw, of the second ethylene-based interpolymer (Mw(second)) is from 5% to 400% greater than the Mw of the first ethylene-based interpolymer (Mw(first)). All individual values and subranges from 5 to 400% are included and disclosed herein; for example, the percentage increase of Mw(second) over Mw(first) may range from a lower limit of 5, 10, 20, 50, 100, 200 or 300% to an upper limit of 70, 150, 275, 350 or 400%. For example, the percentage increase of Mw(second) over Mw(first) can be from 5% to 400%, or in the alternative, from 5% to 200%, or in the alternative, from 10% to 400%, or in the alternative; from 20% to 400%, or in the alternative, from 200% to 400%.

The disclosure further provides the first ethylene-based polymer and the composition in accordance with any embodiment disclosed herein except that the ratio of the number average molecular weight of the second ethylene-based interpolymer (Mn(second)) to the number average molecular weight of the first ethylene-based interpolymer (Mn(first)) is from 0.8 to 1.5. All individual values and subranges from 0.8 to 1.5 are included and disclosed herein; for example, the ratio Mn(second)/Mn(first) can range from a lower limit of 0.8, 0.9, 1.0, 1.1, 1.2, 1.3 or 1.4 to an upper limit of 0.9, 1.0, 1.1, 1.2, 1.3, 1.4, or 1.5. For example, the ratio Mn(second)/Mn(first) can be from 0.8 to 1.5, or in the alternative, from 0.8 to 1.2, or in the alternative, from 1.1 to 1.5, or in the alternative, from 1 to 1.3.

As used here, the molecular weight distribution (MWD) means the ratio of the weight average molecular weight, Mw, to the number average molecular weight, Mn. The disclosure further provides the first ethylene-based polymer and the composition in accordance with any embodiment disclosed herein except that the ratio of the MWD of the second ethylene-based polymer (MWD(second) to the MWD of the first ethylene-based polymer (MWD(first))is greater than 1.0. All individual values and subranges greater than 1 are included and disclosed herein. For example, the ratio of MWD(second) to MWD(first) can be greater than 1.0, or in the alternative, greater than 1.1, or in the alternative, greater than 1.2, or in the alternative, greater than 1.5, or in the alternative, greater than 2.0.

In another embodiment, the ratio of the weight average molecular weight of the second ethylene-based interpolymer (Mw(second)) to the weight average molecular weight of the first ethylene-based interpolymer (Mw(first)) is from equal to or greater than 1.03. All individual values and subranges from equal to or greater than 1.03 are included and disclosed herein. For example, the ratio of the weight average molecular weight of the second ethylene-based interpolymer (Mw (second)) to the weight average molecular weight of the first ethylene-based interpolymer (Mw(first)) is from equal to or greater than 1.03, or in the alternative, equal to or greater than 1.1, or in the alternative, equal to or greater than 1.5, or in the alternative, equal to or greater than 2.0.

The disclosure further provides the composition in accordance with any embodiment disclosed herein except that the density of the second ethylene-based interpolymer has a density from 0.85 to 0.96 g/cc. All individual values and subranges from 0.85 to 0.96 g/cc are included and disclosed herein; for example, the density of the second ethylene-based interpolymer can range from a lower limit of 0.85, 0.87, 0.89, 0.91, 0.93 or 0.95 g/cc to an upper limit of 0.86, 0.88, 0.90, 0.92, 0.94 or 0.96 g/cc. For example, the density of the second ethylene-based interpolymer can be from 0.85 to 0.96 g/cc, or in the alternative, from 0.85 to 0.91 g/cc, or in the alternative, from 0.90 to 0.96 g/cc, or in the alternative, from 0.86 to 0.94 g/cc.

The disclosure further provides the composition in accordance with any embodiment disclosed herein except that the second ethylene-based polymer comprises, in polymerized form, greater than 60 wt % monomer units derived from ethylene, based on the total weight of the second ethylene-based polymer. All individual values and subranges from greater than 60 wt % are included and disclosed herein. For example, the second ethylene-based polymer may comprise, in polymerized form, greater than 60 wt % monomer units derived from ethylene, or in the alternative, greater than 70 wt % monomer units derived from ethylene, or in the alternative, greater than 80 wt % monomer units derived from ethylene, or in the alternative, greater than 90 wt % monomer units derived from ethylene, or in the alternative, greater than 98 wt % monomer units derived from ethylene, or in the alternative, greater than 99 wt % monomer units derived from ethylene, or in the alternative, greater than 99.7 wt % monomer units derived from ethylene, all based on the weight of the second ethylene-based polymer.

The disclosure further provides the composition in accordance with any embodiment disclosed herein except that the second ethylene-based polymer comprises, in polymerized form, from 0.04 to 0.60 wt % monomer units derived from VBCB. All individual values and subranges from 0.04 to 0.60 wt % are included and disclosed herein; for example, the amount of units derived from VBCB, in polymerized form may range from a lower limit of 0.04, 0.05, 0.1, 0.15, 0.2, 0.25, 0.35, 0.45 or 0.55 wt % to an upper limit of 0.05, 0.1, 0.15, 0.2, 0.25, 0.3, 0.40, 0.50 or 0.60 wt %. For example, the second ethylene-based polymer comprises, in polymerized form, from 0.04 to 0.60 wt % monomer units derived from VBCB, or in the alternative, from 0.1 to 0.2 wt % monomer units derived from VBCB, or in the alternative, from 0.05 to 0.20 wt % monomer units derived from VBCB, or in the alternative, from 0.25 to 0.3 wt % monomer units derived from VBCB.

The disclosure further provides the composition in accordance with any embodiment disclosed herein except that the second ethylene-based polymer comprises, in polymerized form, from 0.005 to 0.070 mole % monomer units derived from VBCB. All individual values and subranges from 0.005 to 0.070 mole % are included and disclosed herein; for example, the amount of monomer units, in polymerized form, derived from VBCB may range from a lower limit of 0.005, 0.01, 0.015, 0.02, 0.025, 0.035, 0.045, 0.055 or 0.065 mole % to an upper limit of 0.01, 0.015, 0.02, 0.025, 0.03, 0.040, 0.050, 0.060 or 0.70 mole %. For example, the second ethylene-based polymer comprises, in polymerized form, from 0.005 to 0.070 mole % monomer units derived from VBCB, or in the alternative, from 0.005 to 0.045 mole %, or in the alternative, from 0.035 to 0.070 mole %, or in the alternative, from 0.02 to 0.06 mole %.

In a particular embodiment, the second ethylene-based interpolymer is made according to the reaction scheme shown below:

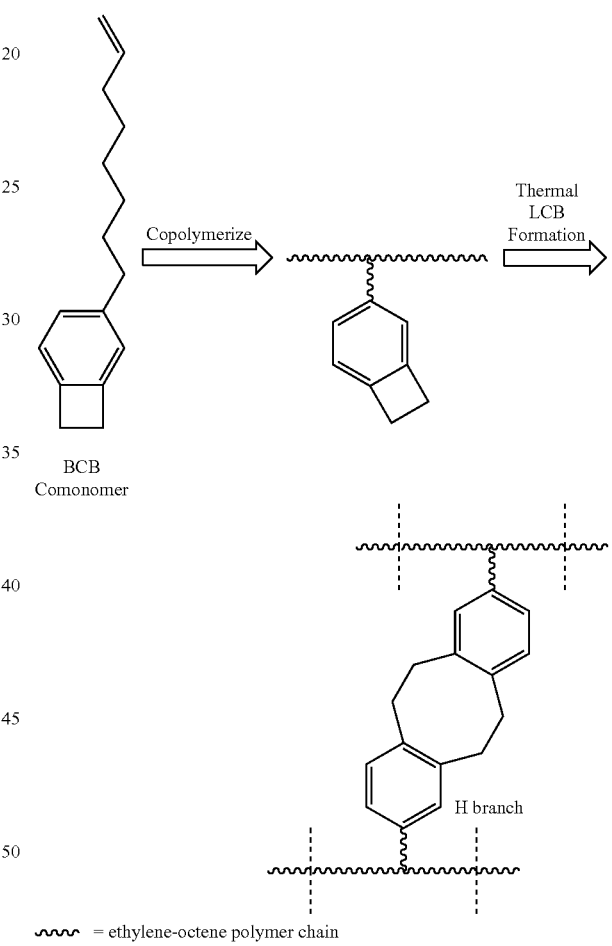

$\sim\sim\sim$ = ethylene-octene polymer chain wherein the vinyl benzocyclobutene (BCB Comonomer in the reaction scheme above) is copolymerized with an ethylene and 1-octene and then subjected to thermal treatment to induce long chain branching formation.

The copolymerization of ethylene and VBCB monomer and optionally one or more alpha-olefins may be catalyzed by a single site catalyst, including for example, constrained geometry catalysts (CGC), bis-biphenylphenoxy type catalysts, and bis-metallocene catalysts, and further constrained geometry catalysts (CGC), bis-biphenylphenoxy type catalysts. In a particular embodiment, the copolymerization is catalyzed by the catalyst shown in the Structure below:

Structure 2

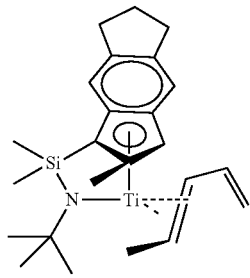

The copolymerization may be further conducted in the presence of a co-catalyst, such as (bis-hydrogenatedtallowalkylmethylammonium tetrakis-pentafluorophenylborate).

In a particular embodiment, the amount of vinyl benzocyclobutene used in the initial copolymerization reaction is controlled such that the resulting branched second ethylene-based interpolymer is completely soluble in tri-chloro-benzene at 160° C.

In the structures above, the notation "∿∿" represents —(CH2-CH2)n-.

In one embodiment, the first composition comprises the first ethylene-based interpolymer. In yet another embodiment, the first composition comprises one or more additives.

In another embodiment, the disclosure provides an article formed from the first composition.

Additives

An inventive composition may comprise one or more additives. Additives include, but are not limited to, stabilizers, plasticizers, antistatic agents, pigments, dyes, nucleating agents, fillers, slip agents, fire retardants, processing aids, smoke inhibitors, viscosity control agents and anti-blocking agents. The polymer composition may, for example, comprise less than 10 percent of the combined weight of one or more additives, based on the weight of the inventive polymer.

In one embodiment the polymers of this invention are treated with one or more stabilizers, for example, antioxidants, such as IRGANOX 1010, IRGANOX 1076 and IRGAFOS 168. In general, the polymers are treated with one or more stabilizers before extrusion or other melt processes.

An inventive composition may further comprise at least one other polymer, in addition to an inventive ethylene-based polymer. Blends and mixtures of the inventive polymer with other polymers may be prepared. Suitable polymers for blending with the inventive polymers include natural and synthetic polymers. Exemplary polymers for blending include propylene-based polymers (both impact modifying polypropylene, isotactic polypropylene, atactic polypropylene, and random propylene/ethylene copolymers), various types of ethylene-based polymers, including high-pressure, free-radical LDPE, heterogeneously branched LLDPE (typically via Ziegler-Natta catalysis), homogeneously branched linear or substantially linear PE (typically via single-site, including metallocene catalysis), including multiple reactor PE ("in-reactor" compositions of heterogeneously branched PE and homogeneously branched PE, such as products disclosed in U.S. Pat. No. 6,545,088 (Kolthammer et al.); U.S. Pat. No. 6,538,070 (Cardwell, et al.); U.S. Pat. No. 6,566,446 (Parikh, et al.); U.S. Pat. No. 5,844,045 (Kolthammer et al.); U.S. Pat. No. 5,869,575 (Kolthammer et al.); and U.S. Pat. No. 6,448,341 (Kolthammer et al.)), ethylene-vinyl acetate (EVA), ethylene/vinyl alcohol copolymers, polystyrene, impact modified polystyrene, ABS, styrene/butadiene block copolymers and hydrogenated derivatives thereof (SBS and SEBS), and thermoplastic polyurethanes. Other ethylene-based polymers include homogeneous polymers, such as olefin plastomers and elastomers (for example, polymers available under the trade designations AFFINITY Plastomers and ENGAGE Elastomers (The Dow Chemical Company) and EXACT (ExxonMobil Chemical Co.)). Propylene-based copolymers (for example, polymers available under the trade designation VERSIFY Plastomers & Elastomers (The Dow Chemical Company) and VISTAMAXX (ExxonMobil Chemical Co.) can also be useful as components in blends comprising an inventive polymer.

Applications

The polymers of this invention may be employed in a variety of conventional thermoplastic fabrication processes to produce useful articles, including monolayer and multilayer films; molded articles, such as blow molded, injection molded, or rotomolded articles; coatings; fibers; and woven or non-woven fabrics.

Other suitable applications include, but are not limited to, wires and cables, gaskets and profiles, adhesives; footwear components, and auto interior parts.

In a particular embodiment, the disclosure provides an article formed from any embodiment of the first composition.

DEFINITIONS

Unless stated to the contrary, implicit from the context, or customary in the art, all parts and percents are based on weight, and all test methods are current as of the filing date of this application.

The term "composition," as used herein, includes a mixture of materials which comprise the composition, as well as reaction products and decomposition products formed from the materials of the composition.

The term "polymer" refers to a compound prepared by polymerizing monomers, whether of the same or a different type. The generic term polymer thus embraces the term homopolymer (which refers to polymers prepared from only one type of monomer with the understanding that trace amounts of impurities can be incorporated into the polymer structure), and the term "interpolymer" as defined below. Trace amounts of impurities may be incorporated into and/or within the polymer.

The term "interpolymer" refers to polymers prepared by the polymerization of at least two different types of monomers. The generic term interpolymer includes copolymers (which refers to polymers prepared from two different monomers), and polymers prepared from more than two different types of monomers.

The term "ethylene-based polymer" refers to a polymer that comprises a majority amount of polymerized ethylene, based on the weight of the polymer, and, optionally, may comprise at least one comonomer.

The term "ethylene-based interpolymer" refers to an interpolymer that comprises a majority amount of polymerized ethylene, based on the weight of the interpolymer, and comprises at least one comonomer.

The term "ethylene-based copolymer" refers to an copolymer that comprises a majority amount of polymerized ethylene, based on the weight of the interpolymer, and a comonomer, as the only monomer types.

The term "ethylene/α-olefin interpolymer," as used herein, refers to a polymer that comprises, in polymerized form, a majority weight percent of ethylene (based on the weight of the interpolymer), and at least one a-olefin.

The term, "ethylene/a-olefin copolymer," as used herein, refers to a copolymer that comprises, in polymerized form, a majority amount of ethylene monomer (based on the weight of the copolymer), and an a-olefin, as the only two monomer types.

The term "propylene-based polymer" refers to a polymer that comprises a majority amount of polymerized propylene, based on the weight of the polymer, and, optionally, may comprise at least one comonomer.

The term "thermally treating," as used herein, refers to the application of heat to a material or composition. Heat may be applied using, for example, heat conduction through different forms of electrical heating devices, through oil or water jacketed barrels, and/or through viscous dissipation in a mechanical mixer.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed.

All molecular weights discussed herein are absolute. That is, Mw is Mw(abs) and Mn is Mn(abs), and Mz is Mz(abs), as those terms are commonly understood.

TEST METHODS

Density

Samples that were measured for density were prepared according to ASTM D 1928. Samples were pressed at 374° F. (190° C.), and 30,000 psi, for three minutes, and then at 70° F. (21° C.) and 30,000 psi for one minute. Density measurements were made within one hour of sample pressing, using ASTM D792, Method B.

Melt Index

Melt index, or I2, was measured in accordance by ASTM D 1238, Condition 190° C./2.16 kg, and was reported in grams eluted per 10 minutes. The I10 was measured in accordance with ASTM D 1238, Condition 190° C/10 kg, and was reported in grams eluted per 10 minutes.

GPC Method: Triple Detector Gel Permeation Chromatography (TDGPC)—Conventional GPC Data—A Triple Detector Gel Permeation Chromatography (3D-GPC or TDGPC) system consisting of a Polymer Laboratories (now Agilent) high temperature chromatograph Model 220, equipped with a 2-angle laser light scattering (LS) detector Model 2040 (Precision Detectors, now Agilent), an IR-4 infra-red detector from Polymer Char (Valencia, Spain), and a 4-capillary solution viscometer (DP) (Visotek, now Malvern) is used. Data collection is performed using Polymer Char DM 100 data acquisition box and related software (Valencia, Spain). The system is also equipped with an online solvent degassing device from Polymer Laboratories (now Agilent).

High temperature GPC columns consisting of four 30 cm, 20 um mixed A LS columns from Polymer Laboratories (now Agilent) are used. The sample carousel compartment is operated at 140° C., and the column compartment is operated at 150° C. The samples are prepared at a concentration of 0.1 grams of polymer in 50 milliliters of solvent. The chromatographic solvent and the sample preparation solvent is 1,2,4-trichlorobenzene (TCB) containing 200 ppm of 2,6-di-tert-butyl-4methylphenol (BHT). The solvent is sparged with nitrogen. The polymer samples are gently stirred at 160° C. for four hours. The injection volume is 200 microliters. The flow rate through the GPC is set at 1.0 ml/minute.

Column calibration and sample molecular weight calculations are performed using Polymer Char "GPC One" software. Calibration of the GPC columns is performed with 21 narrow molecular weight distribution polystyrene standards. The molecular weights of the polystyrene standards range from 580 to 8,400,000 g/mol and are arranged in 6 "cocktail" mixtures with at least a decade of separation between the individual molecular weights.

The peak molecular weights of polystyrene standards are converted to polyethylene molecular weights using the following equation (as described in Williams and Ward, J. Polym. Sci., Polym. Let., 6, 621 (1968)): $M_{polyethylene} = A (M_{polystyrene})^B$, here, B has a value of 1.0, and the experimentally determined value of A is around 0.38 to 0.44.

The column calibration curve is obtained by fitting a first order polynomial to the respective polyethylene-equivalent calibration points obtained from the above equation to the observed elution volumes.

The conventional number and weight-average molecular weights (Mn(conv) and Mw(conv), respectively) are calculated according to the following equations:

$$\overline{Mn} = \frac{\sum_i Wf_i}{\sum_i \left(\frac{Wf_i}{M_i}\right)} \qquad \overline{Mw} = \frac{\sum_i (Wf_i * M_i)}{\sum_i Wf_i}$$

where, $Wf_i$ is the weight fraction of the i-th component and $M_i$ is the molecular weight of the i-th component. The molecular weight distribution (MWD) is expressed as the ratio of the weight average molecular weight (Mw) to the number average molecular weight (Mn).

The A value is determined by adjusting the A value in the Williams and Ward Equation until Mw, the weight average molecular weight, calculated using the above Equation, and the corresponding retention volume polynomial agreed with the independently determined value of Mw, obtained in accordance with a linear polyethylene homopolymer reference with known absolute weight-average molecular weight of 115,000 g/mol as measured by LALLS in a manner traceable to standard homopolymer polyethylene NBS1475.

The absolute weight average molecular weight (Mw(abs)) are characterized by the LS detector and IR-4 concentration detector using the following equation:

$$Mw(abs) = K_{LS} * \frac{\sum (LS_i)}{\sum (IR_i)}$$

wherein $\Sigma(LS_i)$ is the response area of the LS detector, $\Sigma(IR_i)$ is the response area of the IR-4 detector, and $K_{LS}$ is the instrument constant which was determined using a standard NIST 1475 with known concentration and certificated value for the weight average molecular weight of 52,000 g/mol.

The absolute molecular weight at each elution volume is calculated using the following equation:

$$M_{LS,i} = K_{LS} * \frac{LS_i}{IR_i}$$

wherein $K_{LS}$ is the determined instrument constant, $LS_i$ and $IR_i$ are the LS and IR detector responses of the same i-th elution component.

The absolute number average and zeta average molecular weight are calculated with the following equations:

$$Mn(abs) = K_{LS} \frac{\sum (IR_i)}{\sum (IR_i)/\left(\frac{LS_i}{IR_i}\right)}$$

$$Mz(abs) = K_{LS} \frac{\sum IR_i * \left(\frac{LS_i}{IR_i}\right)^2}{\sum IR_i * \left(\frac{LS_i}{IR_i}\right)}$$

A linear extrapolation was performed on log $M_{LS,\,i}$—elution volume plot when the log $M_{LS,\,i}$ data scattered caused by low LS or IR detector responses.

Nuclear Magnetic Resonance ($^1$H NMR)

Sample Preparation 3.25 g of tetrachloroethane-$d_2$ (TCE) with 0.001M Cr(AcAc)$_3$ is added to 130 mg of each polymer sample in 10 mm NMR tube. The solution in the tube is purged with $N_2$ for 5 min to reduce the amount of oxygen to reduce the oxidation. The samples are dissolved with the help of a vortexer and a heat block at 110° C.

Data Acquisition Parameters $^1$H NMR was run with a 10 mm single excitation probe at 120° C. on Bruker AVANCE 400 MHz spectrometer. 1H NMR experiment was run with ZG pulse, TD 32768, NS 64, DS 8, SWH 10,000 Hz, AQ 1.64s, D$_1$, 14s.

Data Analysis

Results were calculated by integrating the VBCB NMR spectroscopy resonances at 3.2 ppm to calculate moles of VBCB (MW of 228.4) and area from 3 to −1 ppm to determine total moles of PE. Spectra were referenced to the TCE solvent peak at 6.0 ppm. (see also: Busico et al., Macromolecules 2005, 38, 6988-6996.).

Differential Scanning Calorimetry (DSC)

DSC can be used to measure the melting and crystallization behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. About 5-10 milligram (mg), polymer sample is weighed, and placed in a light aluminum pan (about 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate, and held isothermal at −40° C. for 3 minutes. The sample is then heated to 150° C. (this is the "second heat" ramp) at a 10° C/minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are peak melting temperature ($T_m$), peak crystallization temperature ($T_c$), heat of fusion ($H_f$) (in Joules per gram (J/g)), and the calculated percent (%) crystallinity for polyethylene samples using: % Crystallinity=(($H_f$)/(292 J/g))×100. The heat of fusion ($H_f$) and the peak melting temperature are reported from the second heat curve. Peak crystallization temperature is determined from the cooling curve

EXAMPLES

1) Synthesis of VBCB: 3-(oct-7-en-1-yl)bicyclo[4.2.0]octa-1,3,5-triene

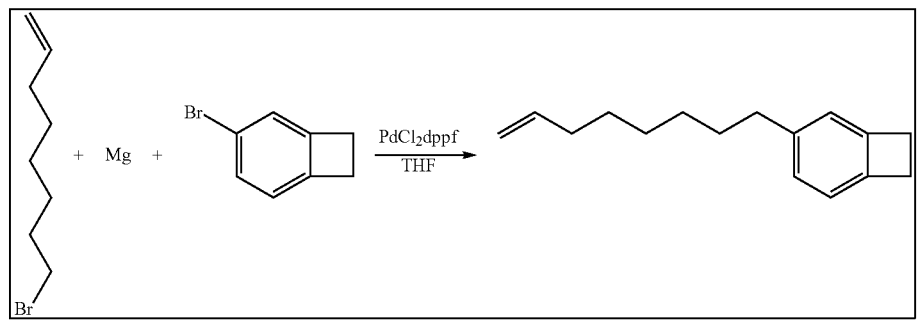

To a 100 mL round bottomed flask was added magnesium turnings and THF. Several drops of 8-bromo-1-octene were added to initiate the reaction. Once the reaction had initiated, a THF solution of the 8-bromo-1-octene was added slowly over the period of 5 minutes. Upon completion of the addition, the mixture was refluxed overnight. This solution/suspension was slowly added to a suspension of the 1-bromobenzocyclobutene and PdCl$_2$dppf (dppf=1,1'-bis(diphenylphosphino)ferrocene) in THF. After addition, the mixture was heated to reflux overnight and the solvent removed by rotary evaporation. The residue was suspended in hexane, and the mixture filtered through a 2 inch pad of silica. The solvent was removed to yield a colorless oil that was purified by column chromatography (5% CH$_2$Cl$_2$ in hexanes) to yield a colorless oil (Yield=62%).

Polymerization

Polymers were produced in a batch reactor, using ethylene and different levels of vinyl benzocyclobutene (VBCB, discussed above), from 0 to 0.42 grams. The reactor was loaded with 1325 g ISOPAR-E hydrocarbon solvent, 20 mmol hydrogen and the appropriate amount of vinyl benzocyclobutene comonomer, before being heated to 150° C., and pressurized with ethylene to 210 psi. When the reactor was at pressure, the polymerization was initiated by adding a catalyst mixture of 1.90 micromoles of the catalyst shown in Structure 2 above, 2.2 micromoles (bis-hydrogenatedtallowalkylmethylammonium tetrakis-pentafluorophenylborate) cocatalyst and 19 micromoles MMAO-3A second cocatalyst. Copolymerization was allowed to proceed for 10 minutes, while maintain reactor temperature and pressure. After the reaction was completed, the polymer was collected by filtration and dried in a vacuum oven overnight before being analyzed. ISOPAR-E is a synthetic isoparaffin which is commercially available from ExxonMobil Chemical Company (Bayport, Tex., USA). The co-catalyst is commercially available from Boulder Scientific Company (Longmont, Colo., USA). MMAO-3A is modified methylaluminoxane, type 3A, which is commercially available from Akzo Nobel Company (Amsterdam, the Netherlands).

Figure 2:
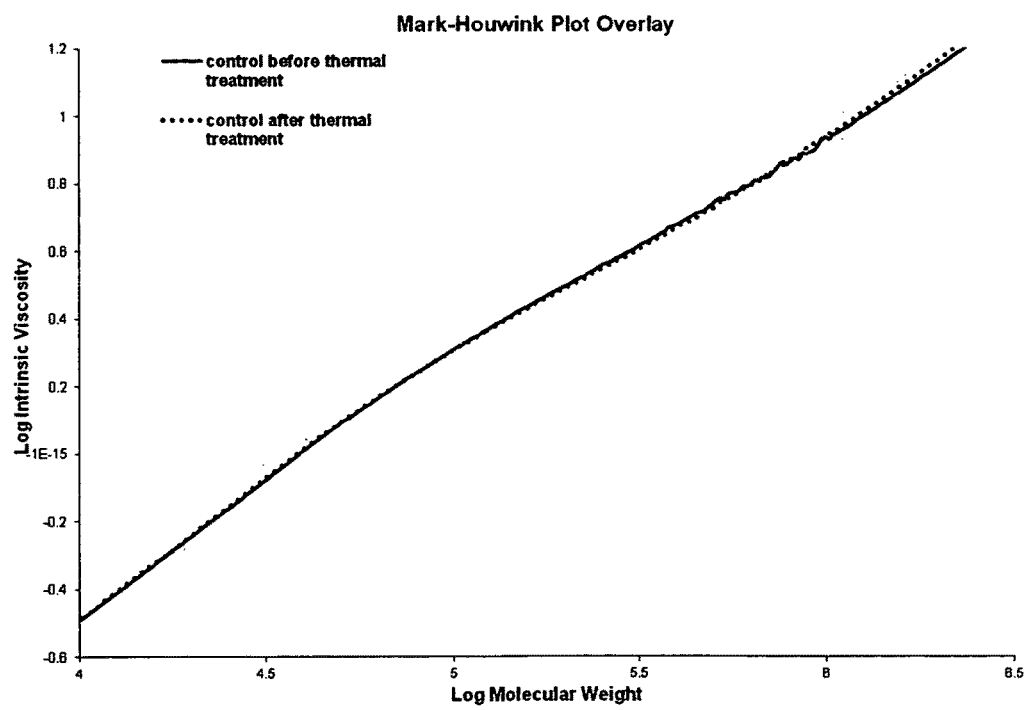
FIG. 2 is a Mark Houwink overlay of the control sample before and after thermal treatment.
Figure 3:
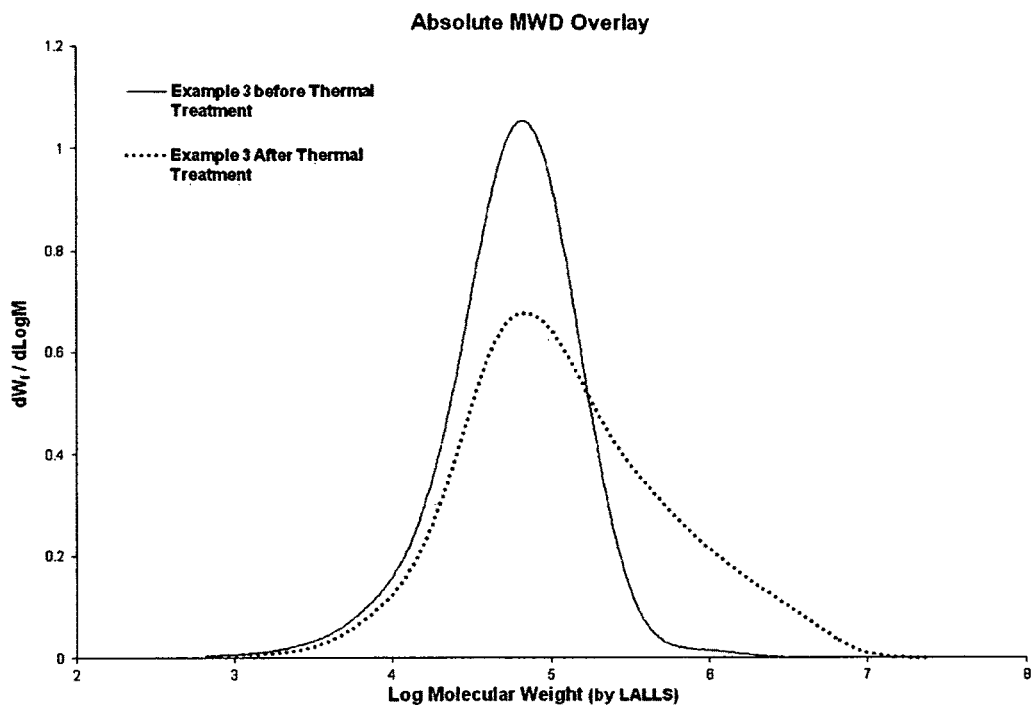
FIG. 3 is a gas phase chromatography overlay of the Inventive Example 3 before and after thermal treating.
Figure 4:
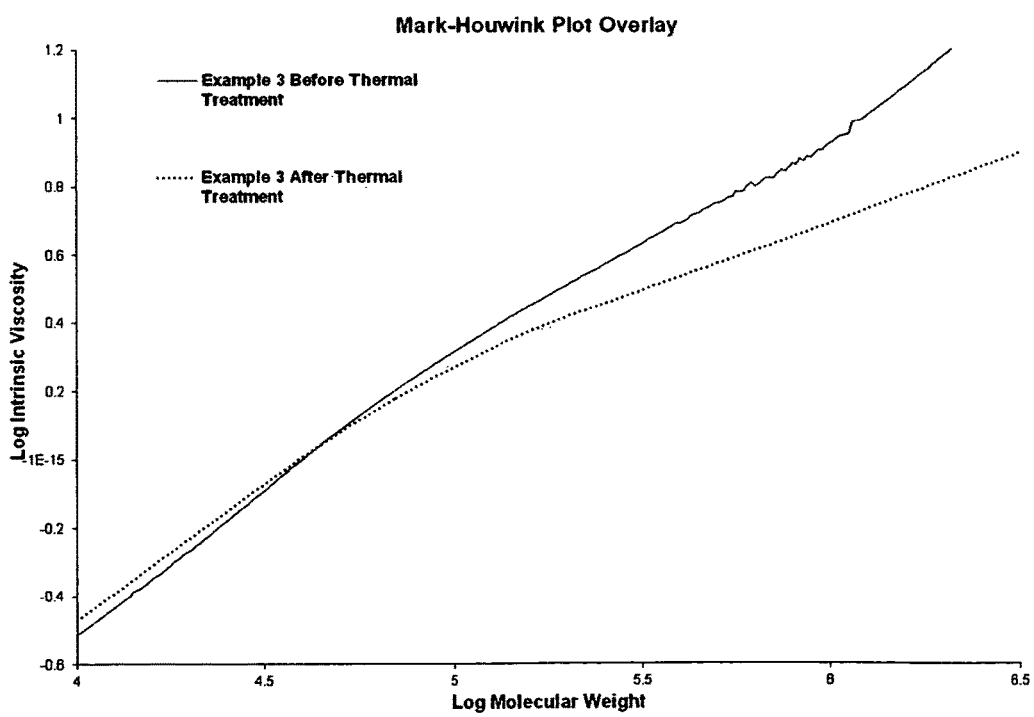
FIG. 4 is a Mark Houwink overlay of Inventive Example 3 before and after thermal treatment.

The molecular weights of the polymers produced in the reactor prior to thermal treatment were independent of the amount of VBCB added, and the resulting molecular weight distributions were relatively narrow (See Table 1, Mw and Mn prior to heating). After thermally treating, the control polymer without any VBCB at 200° C., the molecular weight, molecular weight distribution and amount of branching remained virtually unchanged, as can be seen in Table 1 and FIG. 1, and the amount of branching also remains unchanged, as observed in the Mark-Houwink plot in FIG. 2. In the Inventive Examples with increased VBCB levels, it can be observed that after thermal treatment, the weight average molecular weights and molecular weight distributions are increased significantly, indicative of branch formation in the polymer. The increased molecular weight and increased branching can be observed visually in FIGS. 3 and 4 for Example 3, before, and after, thermal treatment.

2) Thermal Treating Procedure

Each ethylene-based polymer (about 2 grams) was thermally treated in glass vials, by heating in a nitrogen padded oven at 200° C. for 4 hours. After heating, the samples were allowed to cool, without being exposed to oxygen, before being removed from the oven and analyzed.

TABLE 1

|  | Control | Inv. Ex. 1 | Inv. Ex. 2 | Inv. Ex. 3 |
|---|---|---|---|---|
| g VBCB added | 0 | 0.100 | 0.212 | 0.420 |
| Wt % VBCB in final polymer by 1H NMR (based on wt of final polymer) | ND | 0.06 | 0.15 | 0.2 |
| Mole % VBCB in final polymer by 1H NMR (based on total moles of polymerized monomers in final polymer) | ND | 0.0073 | 0.018 | 0.0240 |
| VBCB per 1000 C. by 1H NMR | ND | 0.0368 | 0.0919 | 0.123 |

TABLE 1-continued

|  | Control | Inv. Ex. 1 | Inv. Ex. 2 | Inv. Ex. 3 |
|---|---|---|---|---|
| Polymer made (g) | 23.7 | 21.1 | 19.8 | 17.5 |
| Mw(abs) before heating (g/mol) | 89,183 | 88,278 | 85,580 | 88,512 |
| Mn before heating (g/mol) | 32,103 | 32,597 | 32,095 | 31,620 |
| Mw/Mn (first)* | 2.78 | 2.71 | 2.67 | 2.80 |
| Mw after heating (g/mol) | 89,954 | 92,911 | 109,662 | 259,775 |
| Mn after heating (g/mol) | 32,652 | 31,850 | 35,034 | 41,444 |
| Mw/Mn (second)** | 2.75 | 2.92 | 3.13 | 6.26 |
| Mw (second)/Mw(first)*** | 1.01 | 1.05 | 1.28 | 2.93 |
| Mn (second)/Mn(first) | 1.02 | 0.98 | 1.09 | 1.28 |
| MWD(second)/MWD(first) | 0.99 | 1.08 | 1.17 | 2.24 |

*Mw/Mn before heating.
**Mw/Mn after heating
***Mw after heating divided by Mw before heating.

The invention claimed is:

1. A first ethylene-based interpolymer comprising, in polymerized form, monomer units derived from ethylene and from a benzocyclobutene (VBCB) structure of Structure 1:

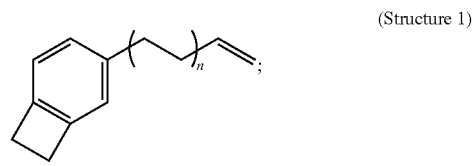

(Structure 1)

wherein n is from 3 to 10; and
wherein the ethylene-based interpolymer comprises, in polymerized form, from 0.02 to 0.70 wt % of the Structure 1, based on the weight of the first ethylene-based interpolymer, as determined by $^1$H NMR; and
wherein the first ethylene-based interpolymer comprises greater than 99 wt % units, in polymerized form, derived from ethylene, based on the weight of the first ethylene-based interpolymer.

2. The first ethylene-based interpolymer of claim 1, wherein the first ethylene-based interpolymer has an absolute weight average molecular weight from 20,000 to 150,000 g/mole.

3. The first ethylene-based interpolymer of claim 1, wherein the first ethylene-based interpolymer has an absolute weight average molecular weight from 80,000 to 100,000 g/mole.

4. A composition comprising:
a first ethylene-based interpolymer comprising, in polymerized form, monomer units derived from ethylene and from a benzocyclobutene (VBCB) structure of Structure 1:

(Structure 1)

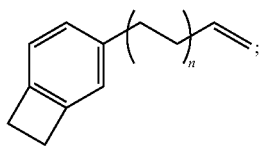

wherein n is from 3 to 10; and wherein the ethylene-based interpolymer comprises, in polymerized form, from 0.02 to 0.70 wt % of the Structure 1, based on the weight of the first ethylene-based interpolymer, as determined by $^1$H NMR; and wherein the first ethylene-based interpolymer is thermally treated to form a second ethylene-based interpolymer.

5. The composition of claim 4, wherein the first ethylene-based interpolymer is thermally treated at a temperature above a melting temperature (as measured by DSC) of the first ethylene-based interpolymer.

6. The composition of claim 5, wherein an Mw(abs) of the second ethylene-based interpolymer is from 5% to 400% greater than an Mw(abs) of the first ethylene-based interpolymer.

7. The composition of claim 4, wherein the second ethylene-based interpolymer has a density from 0.85 to 0.96 g/cc.

8. The composition of claim 4, wherein the second ethylene-based interpolymer comprises the following Structure A (Structure A)

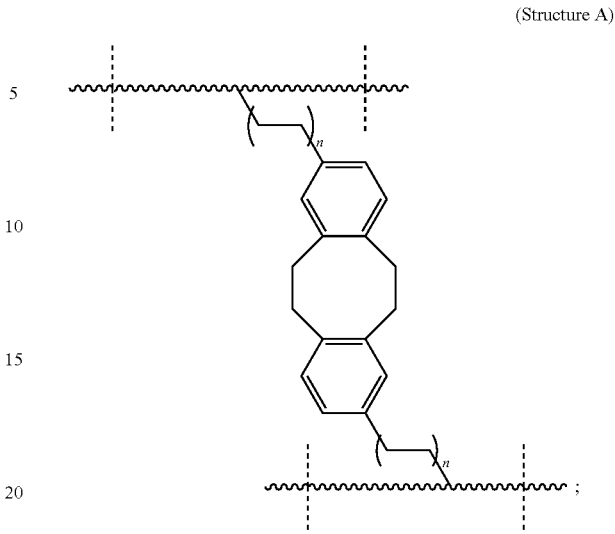

and
wherein each n is independently from 3 to 10.

9. The composition of claim 4, wherein the second ethylene-based interpolymer comprises greater than 60 wt % units, in polymerized form, derived from ethylene, based on the weight of the second ethylene-based interpolymer.

10. The composition of claim 4, wherein the second ethylene-based interpolymer comprises greater than 80 wt % units, in polymerized form, derived from ethylene, based on the weight of the second ethylene-based interpolymer.

11. The composition of claim 4, wherein the second ethylene-based interpolymer comprises greater than 99 wt % units, in polymerized form, derived from ethylene, based on the weight of the second ethylene-based interpolymer.

* * * * *